(12) United States Patent
Gray et al.

(10) Patent No.: US 11,160,960 B2
(45) Date of Patent: Nov. 2, 2021

(54) ANASTOMOTIC DRAINAGE STENT

(71) Applicant: Boston Scientific Scimed, Inc., Maple Grove, MN (US)

(72) Inventors: Jeff Gray, Sudbury, MA (US); Bryan Bannon, Duxbury, MA (US); Ryan R. Donovan, Santa Clara, CA (US); Katharine Eckerline, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 932 days.

(21) Appl. No.: 15/708,647

(22) Filed: Sep. 19, 2017

(65) Prior Publication Data

US 2018/0078745 A1 Mar. 22, 2018

Related U.S. Application Data

(60) Provisional application No. 62/396,524, filed on Sep. 19, 2016.

(51) Int. Cl.
*A61M 27/00* (2006.01)
*A61M 25/04* (2006.01)
*A61B 17/11* (2006.01)
*A61B 1/00* (2006.01)
(Continued)

(52) U.S. Cl.
CPC ....... *A61M 27/002* (2013.01); *A61B 1/00087* (2013.01); *A61B 1/00101* (2013.01); *A61B 17/1114* (2013.01); *A61B 1/012* (2013.01); *A61B 2017/1139* (2013.01); *A61F 2002/041* (2013.01); *A61M 25/04* (2013.01);
(Continued)

(58) Field of Classification Search
CPC ............... A61M 27/002; A61M 25/04; A61M 2205/0216; A61M 2210/1057; A61M 2210/1075; A61B 1/00087; A61B 1/00202; A61B 17/1114; A61B 1/012; A61B 2017/1139; A61F 2002/041
USPC ............................................................. 604/8
See application file for complete search history.

(56) References Cited

U.S. PATENT DOCUMENTS

| 8,454,574 B2 | 6/2013 | Weaver et al. |
| 2004/0193093 A1 | 9/2004 | Desmond |

(Continued)

FOREIGN PATENT DOCUMENTS

| EP | 0716834 A1 | 6/1996 |
| JP | S55161539 U | 11/1980 |

(Continued)

OTHER PUBLICATIONS

"AXIOS Stent", Boston Scientific, http://www.bostonscientific.com/en-US/products/stents--gastrointestinal/axios-stent-and-electrocautery-enhanced-delivery-system.html (Jun. 3, 2016).

(Continued)

*Primary Examiner* — Andrew J Mensh
(74) *Attorney, Agent, or Firm* — Kacvinsky Daisak Bluni PLLC

(57) ABSTRACT

The present disclosure relates to the field of body lumen drainage. Specifically, the present disclosure relates to implantable medical devices for facilitating the flow of fluids and materials between adjacent body lumens. In particular, the present disclosure relates to a drainage stent which maintains an open flow passage between fused tissue layers.

19 Claims, 8 Drawing Sheets

(51) Int. Cl.
*A61F 2/04* (2013.01)
*A61B 1/012* (2006.01)

(52) U.S. Cl.
CPC ............... *A61M 2205/0216* (2013.01); *A61M 2210/1057* (2013.01); *A61M 2210/1075* (2013.01)

(56) References Cited

U.S. PATENT DOCUMENTS

| | | | |
|---|---|---|---|
| 2005/0055039 A1* | 3/2005 | Burnett | A61B 5/14539 606/151 |
| 2005/0177144 A1* | 8/2005 | Phan | A61B 18/1492 606/14 |
| 2008/0243151 A1* | 10/2008 | Binmoeller | A61B 1/041 606/153 |
| 2009/0143713 A1* | 6/2009 | Van Dam | A61M 27/008 604/9 |
| 2014/0012180 A1 | 1/2014 | Levin et al. | |
| 2014/0236064 A1 | 8/2014 | Binmoeller et al. | |
| 2014/0276336 A1* | 9/2014 | Sharma | A61F 5/0089 604/8 |

FOREIGN PATENT DOCUMENTS

| | | |
|---|---|---|
| JP | H03198844 A | 8/1991 |
| JP | 2001500023 A | 1/2001 |
| JP | 2003506132 A | 2/2003 |
| JP | 2009525145 A | 7/2009 |
| WO | 2007140079 A2 | 12/2007 |
| WO | 2012007047 A1 | 1/2012 |
| WO | 2018053477 A1 | 3/2018 |

OTHER PUBLICATIONS

International Search Report and Written Opinion for International application No. PCT/US2017/052200, dated Nov. 30, 2017, 13 pages.
IPRP for application No. PCT/US2017/052200, issued on Mar. 19. 2019, 8 pages.

* cited by examiner

ANASTOMOTIC DRAINAGE STENT

CROSS REFERENCE TO RELATED APPLICATIONS

The present application claims the benefit of priority under 35 U.S.C. § 119 to U.S. Provisional Patent Application Ser. No. 62/396,524, filed on Sep. 19, 2016, which is incorporated by reference in its entirety for all purposes.

FIELD

The present disclosure relates to the field of body lumen drainage. Specifically, the present disclosure relates to implantable medical devices for facilitating the flow of fluids and materials between adjacent body lumens. In particular, the present disclosure relates to a drainage stent which maintains an open flow passage between opposed tissue layers.

BACKGROUND

Gallstones and blockages of bile flow from the gallbladder to the common bile duct require approximately 800,000 gallbladder removal surgeries (i.e., cholecystectomy) per year in the United States alone. Currently available drainage stents may not be indicated for permanent implantation within the patient, and relief from chronic gallstones and/or blockage of bile flow will ultimately require surgical intervention.

SUMMARY

In one aspect, the present disclosure provides a drainage conduit, comprising an elongate tubular body defining a first lumen, a proximal retention structure, a distal retention structure, and a cylindrical saddle region extending therebetween. A funnel member may be attached to a distal end of the elongate tubular body, wherein the funnel member may be configured to move between a first configuration and a second configuration, and wherein, when in the first configuration, the funnel member and elongate tubular body may define an open central lumen to provide a flow path therethrough. The funnel member may fold back along an outer surface of the elongate tubular body when in the second configuration. The funnel member may comprise a compliant or semi-compliant material. The proximal and distal retention structures may extend outward from an outer surface of the elongate tubular body. In addition, or alternatively, the proximal and distal retention structures may extend perpendicular to a circumference of the elongate tubular body. A diameter of the proximal and distal retention structures may be larger than a diameter of the cylindrical saddle region. The proximal and distal retention structures may include opposing planar surfaces configured to contact a surface of opposing tissue walls. The proximal retention structure may be configured to contact a first tissue layer, and the distal retention structure may be configured to contact a second tissue layer. A barrier member may be disposed about portion of the elongate tubular body extending proximally beyond the proximal retention structure. The barrier member may include a mesh-like structure. The drainage conduit may further include a valve disposed within the lumen of the elongate tubular body. The drainage conduit may further comprise a tab extending from an inner surface of the elongate tubular body into the first lumen. The tab may include an aperture therein. The tab may be disposed at a distal end of the elongate tubular body.

In another aspect, the present disclosure provides a drainage system, comprising a tissue anchor defining a first lumen, a proximal retention structure, a distal retention structure, and a cylindrical saddle region extending therebetween, and a funnel member defining a second lumen, wherein the funnel member may include a proximal flange configured to form an interference fit with an inner surface of the distal retention structure, and wherein the tissue anchor and funnel member may define an open central lumen when the proximal flange is disposed within the distal retention structure, thereby providing a flow path therethrough. The funnel member may comprise a compliant or semi-compliant material. The proximal flange may extend perpendicular to a proximal end of the funnel member. A diameter of the proximal flange may be larger than a diameter of the cylindrical saddle region. A valve may be disposed within the second lumen of the funnel member. The tissue anchor may include a self-expanding stent, including, for example a metallic stent.

In yet another aspect, the present disclosure provides a delivery system, comprising an endoscope with a proximal end, a distal end, and a lumen extending therebetween, and a drainage conduit disposed within the lumen of the endoscope. The drainage conduit may include an elongate tubular body defining a first lumen, a proximal retention structure, a distal retention structure, and a cylindrical saddle region extending therebetween. A funnel member may be attached to a distal end of the elongate tubular body, wherein the funnel member may be configured to move between a first configuration and a second configuration, and wherein, when in the first configuration, the funnel member and elongate tubular body may define an open central lumen to provide a flow path therethrough. A tab may extend from an inner surface of the elongate tubular body into the first lumen. The distal end of the endoscope may be disposed within the first lumen of the elongate tubular body and may contact the tab. A tether forming a loop may extend the length of the endoscope lumen and back along an outer surface of the endoscope, wherein the tether may be configured to maintain the funnel member in the second configuration.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures.

Figure 4A:
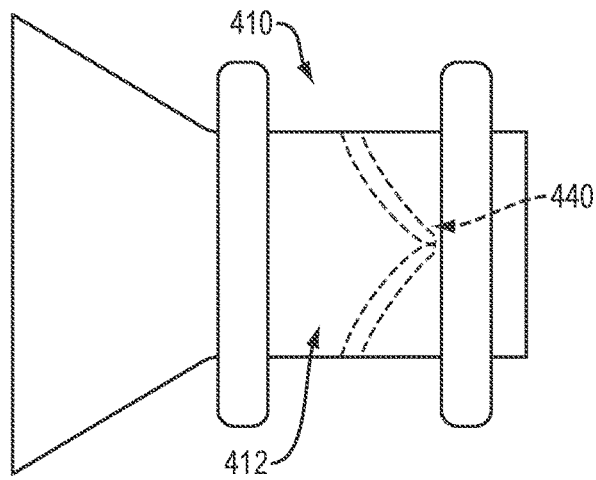
FIGS. 4A-4B illustrate side views of a drainage conduit that includes a one-way duck-bill valve in the closed (FIG.
Figure 4B:
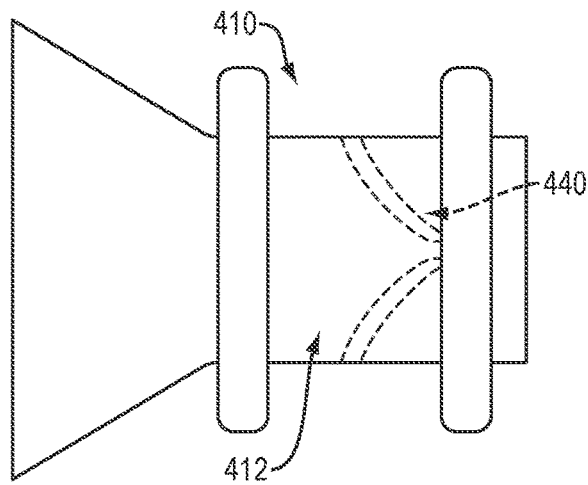

4A) and open (FIG. 4B) configurations, according to an embodiment of the present disclosure.

Figure 5A:
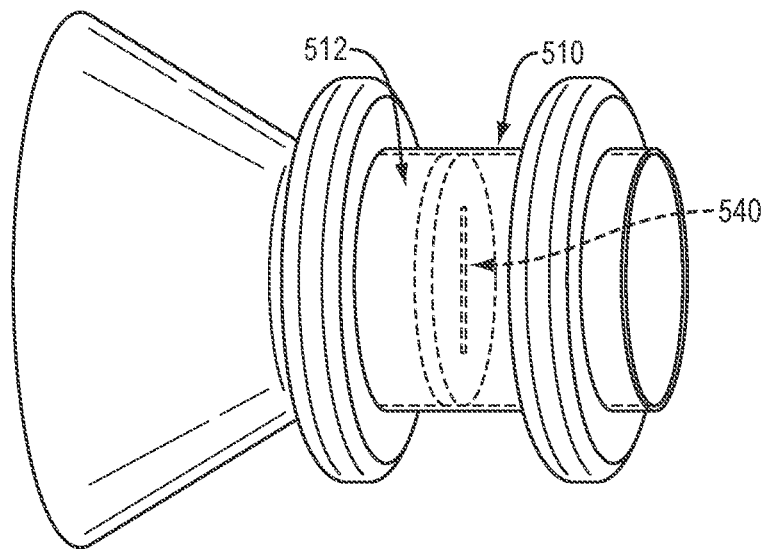
Figure 5B:
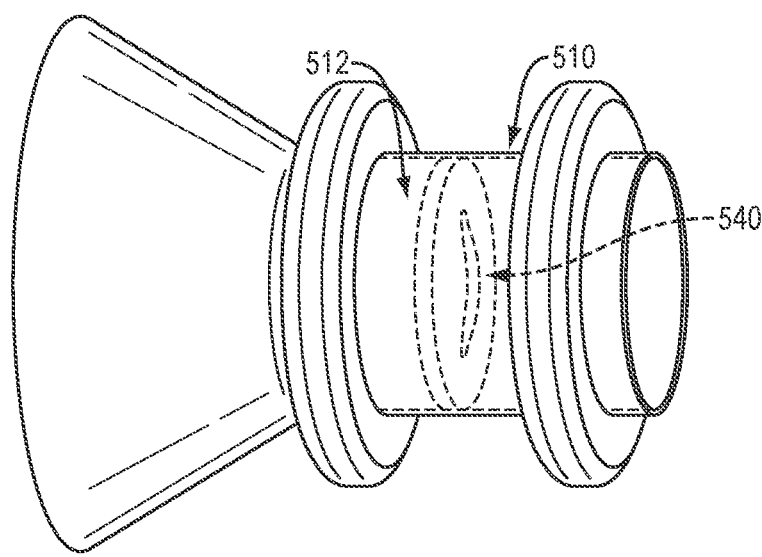

FIGS. 5A-5B illustrate side views of a drainage conduit that includes a one-way pressure slit-valve in the closed (FIG. 5A) and open (FIG. 5B) configuration, according to another embodiment of the present disclosure.

Figure 6A:
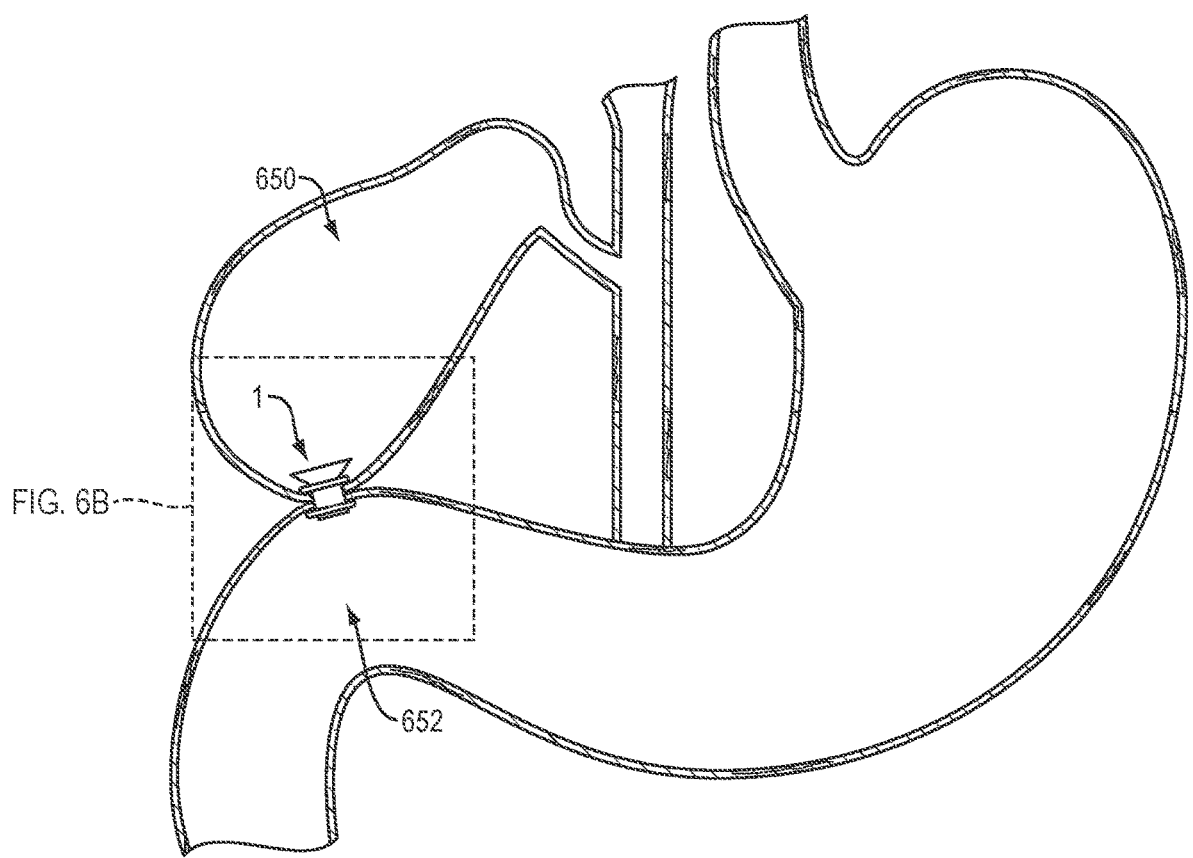
Figure 6B:
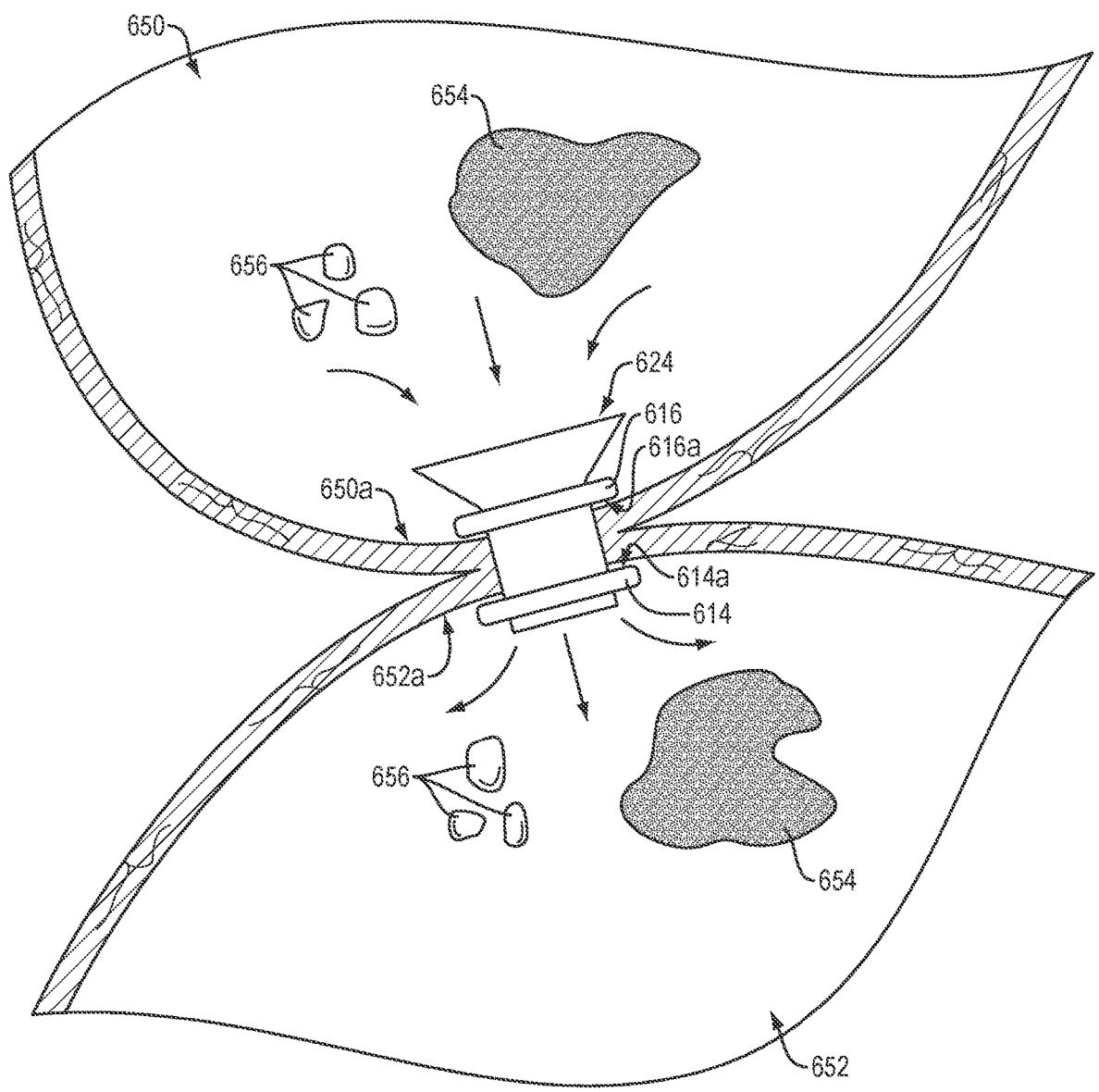

FIGS. 6A-6B illustrate schematic views of a drainage conduit disposed within an anastomosis between the gallbladder and duodenum, according to an embodiment of the present disclosure.

Figure 7A:
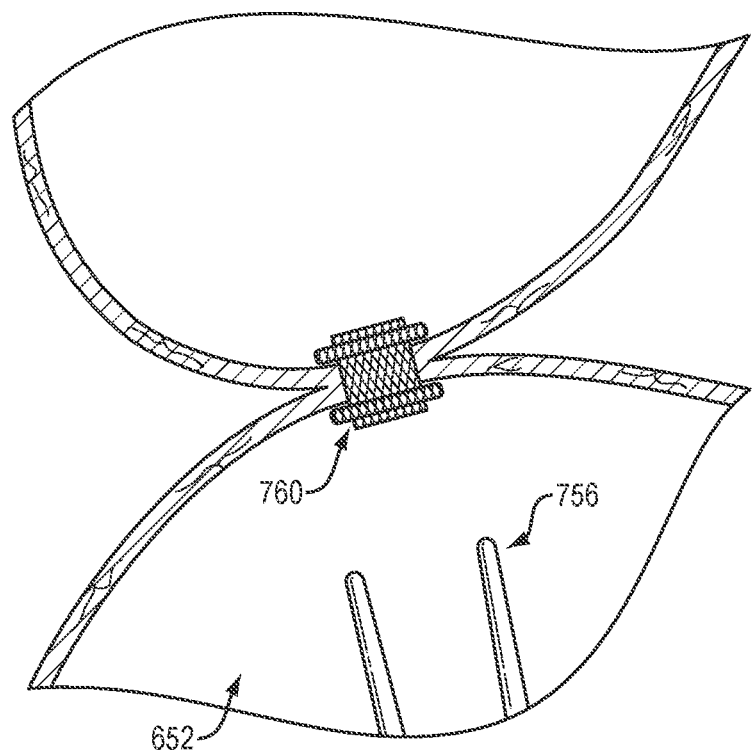
Figure 7B:
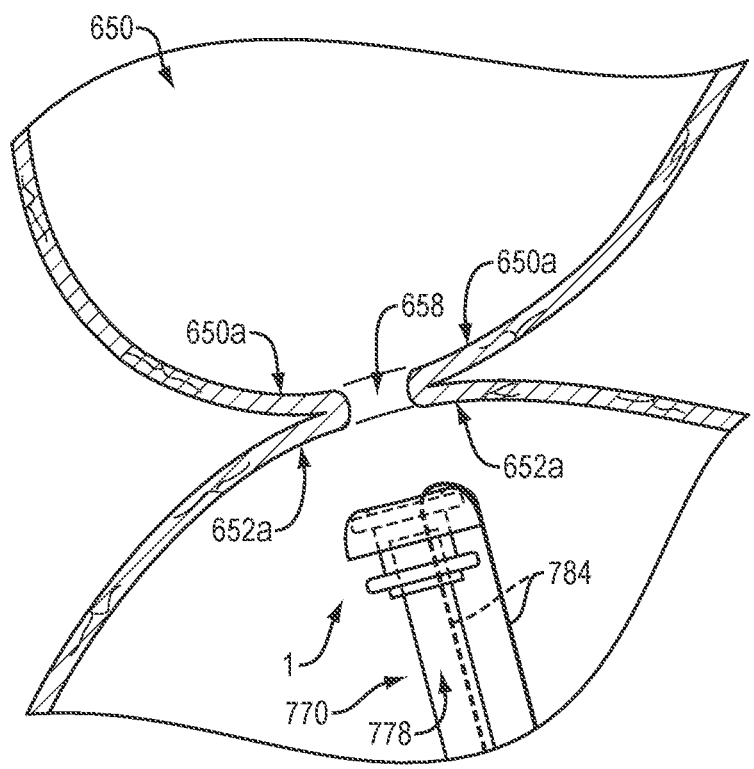
Figure 7C:
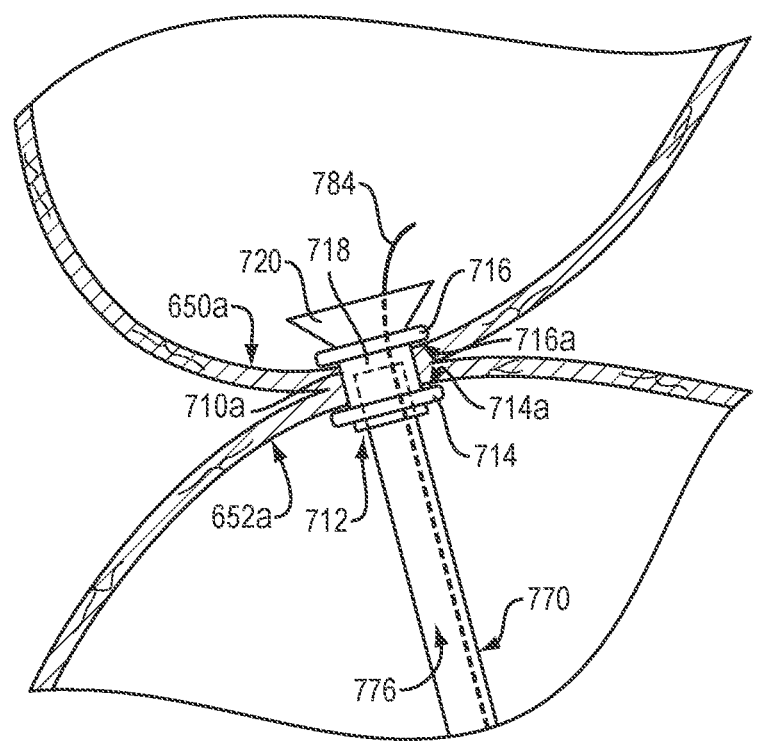

FIGS. 7A-7C illustrate a method for replacing a temporary drainage stent with a drainage conduit, according to an embodiment of the present disclosure.

Figure 8:
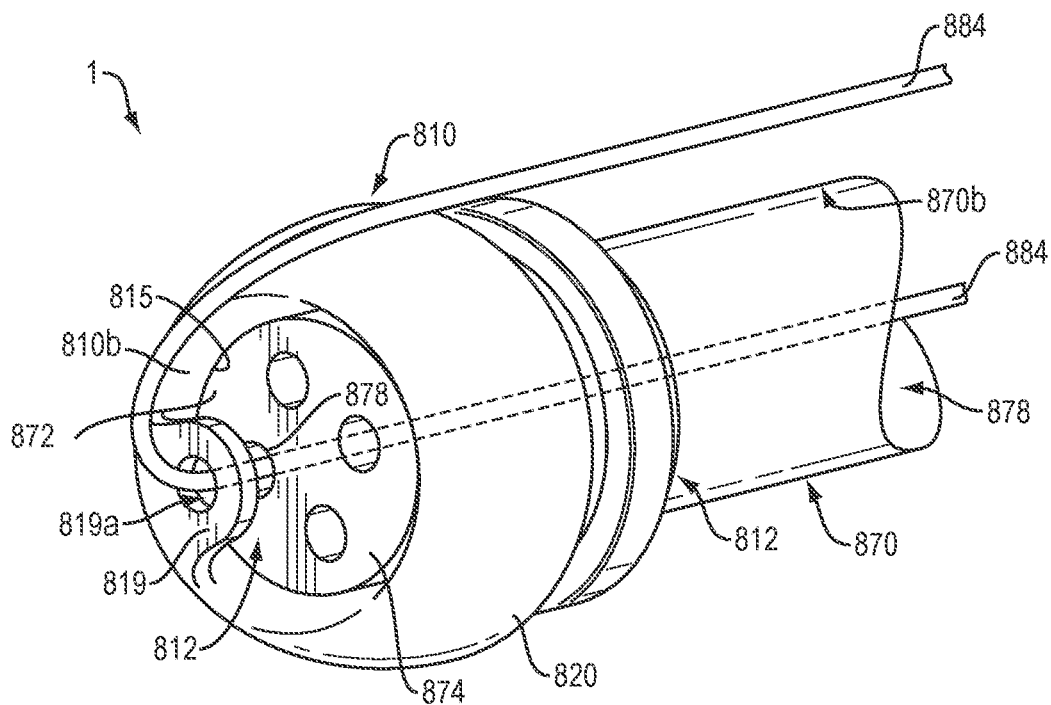

FIG. 8 illustrates a perspective view of a drainage conduit disposed on the distal end of an endoscope in a delivery configuration, according to an embodiment of the present disclosure.

Figure 9A:
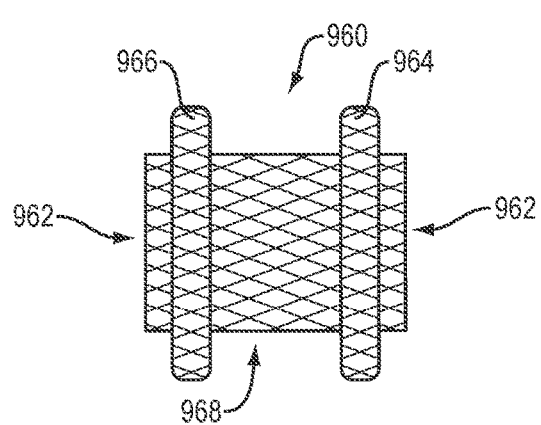
Figure 9B:
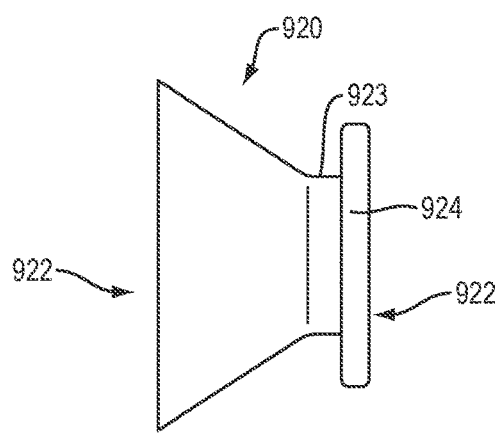
Figure 9C:
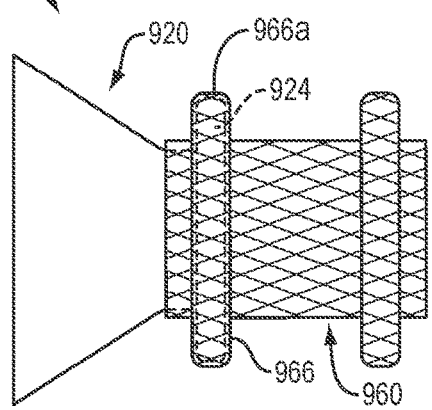

FIGS. 9A-9C illustrate a drainage system, according to another embodiment of the present disclosure.

Figure 10:
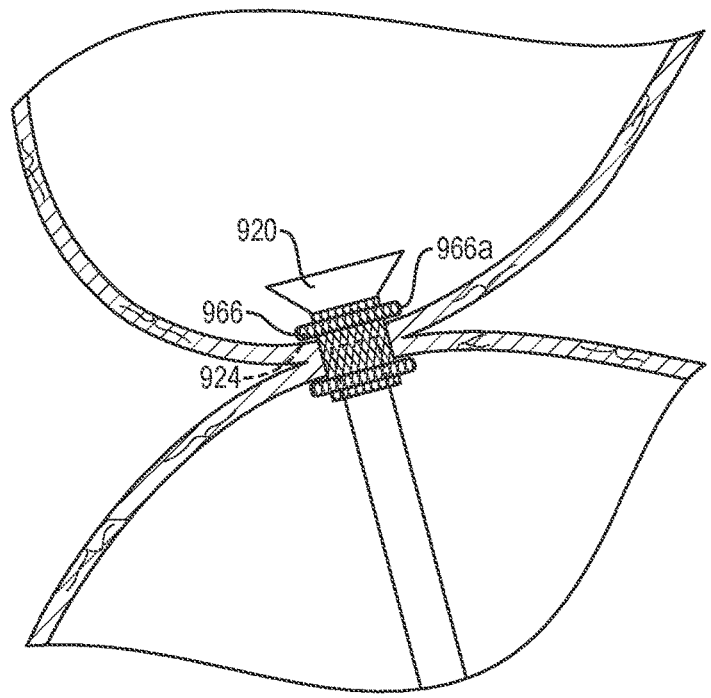

FIG. 10 illustrates the drainage system of FIG. 9C disposed within an anastomosis between the gallbladder and duodenum, according to an embodiment of the present disclosure.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to medical devices and systems for permanent drainage of the gallbladder, it should be appreciated that such medical devices may be used to establish and/or maintain a temporary or permanent anastomosis between a variety of body organs, lumens and spaces, e.g., the stomach and duodenum. Moreover, such medical devices are not limited to drainage, but may facilitate access to organs for other purposes, such as delivering therapy, including non-invasive manipulation of the tissue within the organ and/or the introduction of pharmacological agents via the anastomosis.

As used herein, the term "distal" refers to the end farthest away from a medical professional when introducing a device into a patient, while the term "proximal" refers to the end closest to the medical professional when introducing a device into a patient.

Figure 1A:
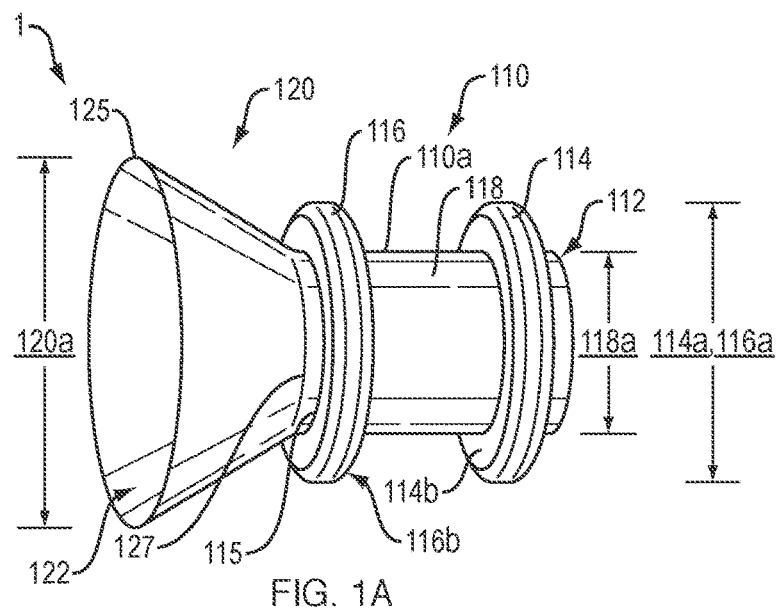
FIGS. 1A-1B illustrate side views of a drainage conduit in the deployed (FIG. 1A) and delivery (FIG. 1B) configurations, according to an embodiment of the present disclosure.

In one embodiment, the present disclosure provides a drainage conduit configured to fit within a previously formed anastomosis between opposed tissue layers. As illustrated in FIG. 1A, the drainage conduit 1 may include an elongate tubular body 110 defining a first lumen 112. The elongate tubular body 110 may include a cylindrical saddle region 118 with proximal and distal retention structures 114, 116 extending outward from an outer surface 110a of the elongate tubular body. The elongate tubular body 110 and proximal and distal retention structures 114, 116 may comprise a variety of non-degradable and biocompatible polymeric materials (e.g., upon exposure to bodily fluids such as bile), including, for example, silicones, rubbers, polyethylenes and thermoplastic elastomers. In one embodiment, the proximal and distal retention structures 114, 116 may be unitarily formed with the elongate tubular body 110 by polymeric extrusion process or injection molding process. In addition, or alternatively, the proximal and distal retention structures 114, 116 may be permanently affixed (i.e., adhered, bonded, attached etc.) to the outer surface 110a of the elongate tubular body 110 using suitable glues, adhesives, resins or other polymer bonding techniques.

Figure 1B:
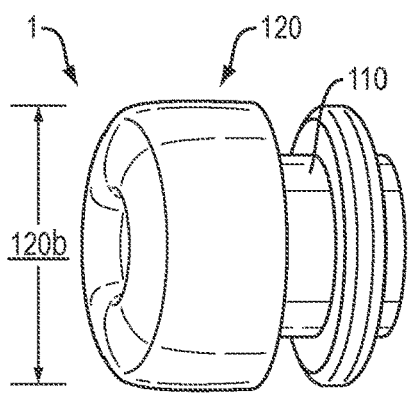

A funnel member 120 may be attached to and extend distally beyond a distal end 115 of the elongate tubular body 110. The funnel member 120 may comprise a sufficiently pliable and/or deformable material to allow the funnel member to move between a first (e.g., deployed) configuration as depicted in FIG. 1A, and a lower-profile second (e.g., delivery) configuration as depicted in FIG. 1B. In one embodiment, the funnel member 120 and elongate tubular body 110 may be formed from the same biocompatible polymeric materials. Alternatively, the funnel member 120 and elongate tubular body may be formed from different biocompatible polymeric materials. For example, the funnel member 120 may comprise a polymeric material that is more compliant that the relatively less compliant polymeric materials of the elongate tubular body 110 and proximal and distal retention structures 114, 116. By way of non-limiting example, the funnel member 120 may include one or more thermoplastics and/or thermosets. Examples of thermoplastics include polyolefins; polyamides (e.g., nylon, such as nylon 12, nylon 11, nylon 6/12, nylon 6, nylon 66); polyesters (e.g., polyethylene terephthalate (PET), polybutylene terephthalate (PBT), polyethylene naphthalate (PEN), polytrimethylene terephthalate (PTT)); polyethers; polyurethanes; polyvinyls; polyacrylics; copolymers and block copolymers thereof, such as block copolymers of polyether and polyamide (e.g., PEBAX®); and mixtures thereof. Examples of thermosets include elastomers (e.g., EPDM), epichlorohydrin, polyureas, nitrile butadiene elastomers and silicones. Biocompatible thermosets may also be used. Biocompatible thermosets include, for example, biodegradable polycaprolactone, poly(dimethylsiloxane) containing polyurethanes and ureas and polysiloxanes.

When in the second configuration (FIG. 1B), the funnel member 120 may fold or roll back to lay against the distal retention structure (not visible) and a portion of the outer surface (not visible) of the elongate tubular body 110. When in the first configuration (FIG. 1A), the funnel member 120 may define a second lumen 122 which is coextensive with the first lumen 112 to form a contiguous open central lumen extending through the drainage conduit 1. In one embodiment, the funnel member 120 may be unitarily formed along with the elongate tubular body 110 by polymeric extrusion process, as is known in the art. In addition, or alternatively, a proximal end 127 of the funnel member may be permanently affixed (i.e., adhered, bonded, attached etc.) to the distal end 115 of the elongate tubular body 110 using suitable glues, adhesives, resins or other polymer bonding techniques, as discussed above. In one embodiment, the funnel member 120 may include a wall thickness that is substantially the same as a wall thickness of the elongate tubular body 110. Alternatively, the funnel member 120 may include a wall thickness that is less than the wall thickness of the elongate tubular body 110. For example, the elongate tubular body 110 may include a wall thickness of approximately 0.5-2.0 mm, and the funnel member 120 may include a wall thickness of approximately 0.1-0.5 mm. In one embodiment, the funnel member 120 may include a variable wall thickness which becomes progressively thinner from the proximal end 127 to the distal end 125 (i.e., as the funnel member increases in diameter).

Referring to FIG. 1A, the proximal and distal retention structures 114, 116 may extend perpendicularly from the outer surface about a circumference (i.e., 360°) of the outer surface 110a of elongate tubular body 110. The proximal and distal retention structures 114, 116 may have an outer diameter 114a, 116a that exceeds the outer diameter 118a of the cylindrical saddle region 118, but which is less than the outer diameter 120a of the funnel member 120 when in the first configuration. For example, the proximal and distal retention structures 114, 116 may have an outer diameter 114a, 116a of approximately 12.0-20.0 mm. The cylindrical saddle region 118 may have an outer diameter 118a of approximately 8.0-12.0 mm diameter, an inner diameter (e.g., first lumen 112) of approximately 6.0-10.0 mm, and a length of approximately 10.0-20.0 mm. The funnel member 120 may have an outer diameter 120a at the distal end 125 of approximately 20.0-50.0 mm when in the first configuration, and an outer diameter 120b approximately equal to the outer diameter 114a, 116a of the proximal and distal retention structures 114, 116 (e.g., approximately 12.0-20.0 mm) when in the second configuration (FIG. 1B). The proximal and distal retention structures 114, 116 may further include opposing planar surfaces 114b, 116b configured to contact the inner surfaces of opposing tissue layers (discussed below). If desired for a particular application, the retention structures may include a diameter that equals or exceeds the diameter of the funnel when deployed.

Figure 2:
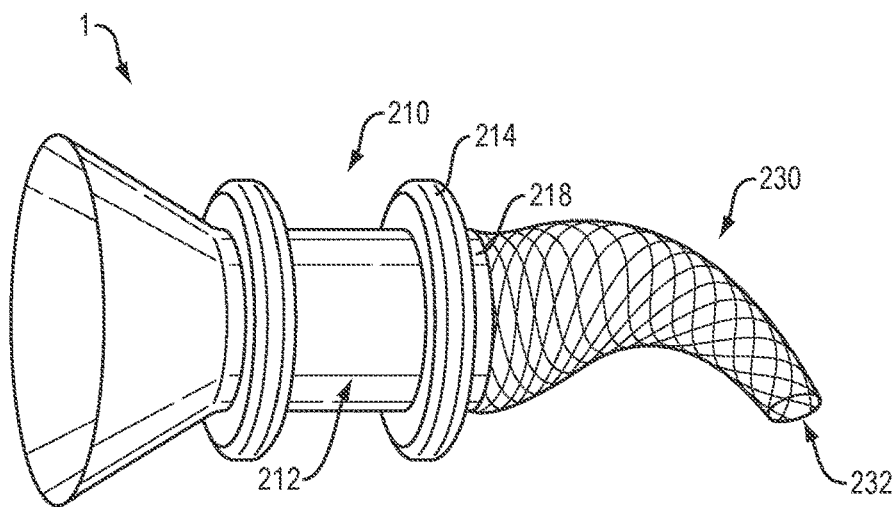
FIG. 2 illustrates a side view of a drainage conduit that includes a barrier member, according to an embodiment of the present disclosure.

Referring to FIG. 2, the drainage conduit 1 may further include a barrier member 230 disposed about a portion of the cylindrical saddle region 218 extending proximally beyond the proximal retention structure 214. The barrier member 230 may include a mesh-like structure comprising a variety of woven or interlaced biocompatible polymers, metals and/or fabrics as are known in the art. The mesh-like structure may include an weaving pattern that provides openings or holes of sufficient size to allow bile and gallstones to pass through, while preventing or inhibiting the flow of digestive material (e.g., food etc.) entering the gallbladder and/or occluding the first lumen 212 of the elongate tubular member 210. It should be appreciated that the flexible composition and tapered design of the mesh-like structure may allow the barrier member 230 to deflect or bend in the direction of flow of digestive materials within the duodenum such that the opening 232 of the barrier member 230 is oriented to prevent or inhibit the entry of digestive materials. It should also be appreciated that the mesh-like structure is sufficiently stretchable to be received over the outer surface of a medical device (e.g., endoscope etc.) without permanently deforming.

Figure 3:
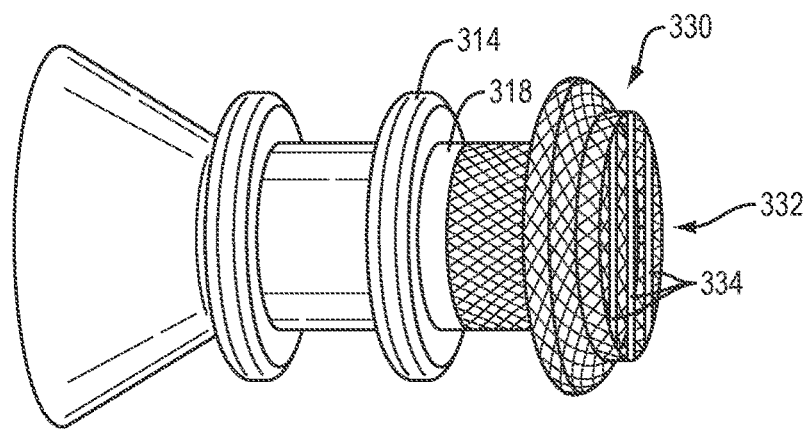
FIG. 3 illustrates a side view of a drainage conduit that includes a barrier member, according to another embodiment of the present disclosure.

Referring to FIG. 3, the barrier member 330 may alternatively include a more rigid mesh-like cap disposed about a portion of the cylindrical saddle region 318 extending proximally beyond the proximal retention structure 314. As above, the barrier member 330 may be comprised of a variety of woven or interlaced biocompatible polymers, metals and/or fabrics as are known in the art. The opening 332 of the barrier member 330 may include a series of longitudinally-spaced bars 334 to prevent or inhibit the entry of digestive materials, as discussed above.

In addition (or as an alternative) to the barrier members, the first lumen 412 of the elongate tubular body 410 may further include a one-way valve 440 (e.g., duck-bill valve) movable between closed (FIG. 4A) and open (FIG. 4B) configurations to further prevent or inhibit the entry of digestive materials, without impeding the flow of bile and/or gallstones. In another embodiment, the first lumen 512 of the elongate tubular body 510 may further include a one-way slit valve 540 movable between closed (FIG. 5A) and open (FIG. 5B) configurations. Examples of such valves are described in U.S. Patent Publication No. 2012/0226243, the contents of which is hereby incorporated by reference in its entirety. Such valves may comprise a variety of suitable biocompatible and non-degradable materials, including any of the polymers discussed herein.

As illustrated in FIG. 6A, the drainage conduit 1 of the present disclosure may be positioned within a pre-formed anastomosis connecting the gallbladder 650 and duodenum 652. Referring to the expanded view of FIG. 6B, the drainage conduit 1 may be positioned within the anastomosis such that the planar surface 616a of the distal retention structure 616 is positioned against or adjacent to the inner wall surface 650a of the gallbladder 650, and the planar surface 614a of the proximal retention structure 614 is positioned against or adjacent to the inner wall surface 652a of the duodenum 652. It should be appreciated that direct contact between the proximal and distal retention structures 614, 616 and the respective tissue wall surfaces 650a, 652a of the gallbladder 650 and duodenum 652 is not necessary to prevent the drainage conduit 1 from moving into the either the gallbladder 650 or duodenum 652. Indeed, in one embodiment, such direct contact is preferably avoided to minimize tissue irritation resulting from prolonged contact with the proximal and distal retention structures 614, 616. As indicated by the direction of the arrows, the open central lumen 624 of the drainage conduit 1 may allow continual flow of gallstones 656 and bile 654 into the duodenum 652 for removal by the body's natural course.

Referring to FIGS. 7A-7C, in practice and by way of example, a previously positioned tissue anchor 760 may be removed using a suitable device, such as grasping member 756, which is advanced through a working channel of an endoscope (not depicted) positioned within the duodenum 652 (FIG. 7A). After the tissue anchor has been removed, an endoscope 770 or other suitable delivery system may be used to advance a drainage conduit 1 in a first configuration to the anastomosis 658 (FIG. 7B). Referring to FIG. 7B, it should be appreciated that the tissue anchor depicted in FIG. 7A was implanted within the patient for a sufficient amount of time, typically 6-9 months, to allow the opposing tissue layers 650a, 652a of the gallbladder 650 and duodenum 652 to fuse and provide a permanent anastomosis 658. The fused tissue layers provide sufficient strength and flexibility to allow the drainage conduit 1 to be gently advanced into the anastomosis without tearing either of the tissue layers. As discussed in greater detail below, the drainage conduit 1 may be maintained in the first delivery configuration using a tether 784 in the form of a simple loop that extends the length of a working channel 778 of the endoscope 770 and back along the outer surface of the endoscope. As illustrated in FIG. 7C, the fused tissue layers 650a, 652a are sufficiently elastic to press and seal against the outer surface 710a of the cylindrical saddle region 718 between the proximal and distal retention structures 714, 716. The opposing planar surfaces 714a, 716a of the proximal and distal retention structures 714, 716 may contact the respective inner wall surfaces 650a, 652a to maintain the drainage conduit 1 within the anastomosis. Still referring to FIG. 7C, with the drainage conduit 1 positioned within the anastomosis, the funnel member 720 may be moved to the first deployed configuration by releasing a first end of the tether 784 and pulling the second end of the tether through a working channel 776 of the endoscope 770. The endoscope 770 may then be retracted proximally and removed from the first lumen 712 of the drainage conduit and withdrawn from the patient.

FIG. 8 provides an enlarged frontal view of the drainage conduit delivery system of FIG. 7B. In one embodiment, the distal end 874 of an endoscope 870 may be disposed within the first lumen 812 of the elongate tubular body 810. The distal end 815 of the elongate tubular body 810 may include a tab 819 that extends from the inner surface 810b into a portion of the first lumen 812. The tab 819 may serve as a stopping member which the distal end 874 of the endoscope 870 may push/press against as the endoscope 870 is advanced through the body passages (e.g., alimentary canal) towards the anastomosis. It should be appreciated that the tab 819 may be sufficiently small that it does not substantially block the flow of fluids and materials through the open central lumen. In addition, the tab 819 may be comprise a sufficiently deformable material such that it folds against the inner surface 810b of the first lumen 812 as fluids and materials flow through the open central lumen.

The tab 819 may further include an aperture 819a configured to receive a tether 884 in the form of a simple loop that extends through a working channel 878 and returns along an outer surface 870b of the endoscope 870. The funnel member 820 may be retained in the second configuration against a portion of the outer surface of the cylindrical saddle region by applying tension to both free ends of the tether 884, which extend beyond the proximal end of the endoscope (not shown). The proximal tension applied to the free ends of the tether 884 also ensures that the distal end 872 of the endoscope 870 remains in contact with the surface of the tab 819 as the delivery system is advanced through the body passages towards the anastomosis. In another embodiment, forceps may be passed through the working channel of the scope, and grasp a tab on the drainage conduit. The scope, drainage conduit, and forceps may all be then advanced in unison to position the drainage conduit into the anastomosis. Once in place, the forceps may be opened (released), thus releasing the drainage conduit. The forceps and scope may then be removed from the drainage conduit.

FIGS. 9A-9C illustrate an alternative embodiment of a drainage system 2, which may include a funnel member 920 configured to be attached to a tissue anchor 960. As illustrated in FIG. 9A, the tissue anchor 960 may include a cylindrical saddle region 968 defining a first lumen 962 with outward extending proximal and distal retention structures 964, 966. As illustrated in FIG. 9B, the funnel member 920 may define a second lumen 922 and include a proximal flange 924 extending outward from a proximal end 923. The funnel member 920 and proximal flange 924 may be comprise a variety of non-degradable and biocompatible polymeric materials, as discussed above. In one embodiment, the funnel member 920 and proximal flange 924 may be unitarily formed by polymeric extrusion process, as is known in the art. In addition, or alternatively, the proximal flange 924 may be permanently affixed (i.e., adhered, bonded, attached etc.) to an outer surface of the funnel member 920 using suitable glues, adhesives, resins or other polymer bonding techniques. As illustrated in FIG. 9C, the proximal flange 924 may be configured to form an interference fit with an inner surface 966a of the distal retention structure 966. The proximal flange 924 may be comprise a sufficiently flexible material that it deforms or collapses as the funnel member 920 is advanced through the first lumen 962 of the tissue anchor 960, and returns to its original shape to expand into and engage the inner surface 966a of the distal retention structure.

As illustrated in FIG. 10, in one embodiment, the funnel member 920 may be disposed in a compressed configuration within the lumen of an endoscope. The endoscope may have an outer diameter which is less than the inner diameter of the first lumen 962, such that the distal end of the endoscope may be positioned within the tissue anchor 960 just proximal to the distal retention structure 966. The funnel member 920 may be deployed from the distal end of the endoscope using e.g., a pushrod slidably disposed within the endoscope lumen. As the funnel member 920 exits the endoscope lumen it may move from the compressed configuration to an expanded (i.e., relaxed) configuration such that the funnel member expands within the gallbladder and the proximal flange engages the inner surface 966a of the distal retention structure 966.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A drainage conduit, comprising:
an elongate tubular body defining a first lumen extending therethrough, the elongate tubular body comprising:
a proximal retention structure,
a distal retention structure, and
a cylindrical saddle region extending therebetween; and
a funnel member attached to a distal end of the distal retention structure,
wherein the funnel member is configured to move between a first configuration and a second configuration,
wherein in the first configuration, the funnel member and elongate tubular body define an open central lumen to provide a flow path therethrough, and
wherein in the second configuration, the funnel member is foldable towards the proximal retention structure to be positioned along an outer surface of the distal retention structure.

2. The drainage conduit of claim 1, wherein the funnel member comprises a compliant or semi-compliant material.

3. The drainage conduit of claim 1, wherein the proximal and distal retention structures extend outward from an outer surface of the elongate tubular body.

4. The drainage conduit of claim 1, wherein the proximal and distal retention structures extend perpendicular to a circumference of the elongate tubular body.

5. The drainage conduit of claim 1, wherein a diameter of the proximal and distal retention structures is larger than a diameter of the cylindrical saddle region, and wherein a distal diameter of the funnel member is larger than a proximal diameter of the funnel member when in the first configuration.

6. The drainage conduit of claim 1, wherein the proximal and distal retention structures include opposing planar surfaces configured to contact a surface of opposing tissue walls.

7. The drainage conduit of claim 1, wherein the proximal retention structure is configured to contact a first tissue layer, and the distal retention structure is configured to contact a second tissue layer.

8. The drainage conduit of claim 1, further comprising a barrier member disposed about a portion of the elongate tubular body extending proximally beyond the proximal retention structure.

9. The drainage conduit of claim 8, wherein the barrier member comprises a mesh of woven or interlaced material.

10. The drainage conduit of claim 1, further including a valve disposed within the first lumen of the elongate tubular body.

11. The drainage conduit of claim 1, further comprising a tab extending from an inner surface of the elongate tubular body into the first lumen.

12. The drainage conduit of claim 11, wherein the tab includes an aperture therein.

13. The drainage conduit of claim 11, wherein the tab is disposed at a distal end of the elongate tubular body.

14. A drainage system, comprising:
a tissue anchor defining a first lumen, the tissue anchor comprising:
a proximal retention structure,
a distal retention structure, and
a cylindrical saddle region extending therebetween; and
a funnel member defining a second lumen, the funnel member comprising a proximal flange configured to form an interference fit with an inner surface of the distal retention structure,
wherein the funnel member is configured to move between a first configuration and a second configuration,
wherein the tissue anchor and funnel member define an open central lumen when the proximal flange is disposed within the distal retention structure, thereby providing a flow path therethrough, and
wherein, when in the second configuration, the funnel member is foldable towards the proximal retention structure to be positioned along an outer surface of the distal retention structure.

15. The drainage system of claim 14, wherein the funnel member comprises a compliant or semi-compliant material.

16. The drainage system of claim 14, wherein the proximal flange extends perpendicular to a proximal end of the funnel member.

17. The drainage system of claim 14, wherein a diameter of the proximal flange is larger than a diameter of the cylindrical saddle region.

18. The drainage system of claim 14, further including a valve disposed within the second lumen of the funnel member.

19. A delivery system, comprising:
a delivery device, comprising:
a proximal end,
a distal end, and
a lumen extending therebetween;
a drainage conduit comprising an elongate tubular body defining a first lumen, the elongate tubular body including a proximal retention structure, a distal retention structure, a cylindrical saddle region extending therebetween, and a funnel member attached to a distal end of the distal retention structure,
wherein the funnel member is configured to move between a first configuration and a second configuration,
wherein in the first configuration, the funnel member and elongate tubular body define an open central lumen to provide a flow path therethrough, and
wherein the funnel comprises a tab extending from an inner surface of the elongate tubular body into the first lumen;
wherein the distal end of the delivery device is disposed within the first lumen of the elongate tubular body and contacts the tab; and
a tether forming a loop which extends the length of the delivery device lumen and back along an outer surface of the delivery device,
wherein the tether is configured to maintain the funnel member in the second configuration.

* * * * *